US005609570A

United States Patent [19]
Lamont

[11] Patent Number: 5,609,570
[45] Date of Patent: Mar. 11, 1997

[54] PROTECTIVE MEDICAL BOOT AND ORTHOTIC SPLINT

[75] Inventor: William D. Lamont, Shelby Township, Mich.

[73] Assignee: LaMed, Inc., Shelby Township, Mich.

[21] Appl. No.: 343,090

[22] Filed: Nov. 21, 1994

Related U.S. Application Data

[63] Continuation-in-part of Ser. No. 90,895, Jul. 12, 1993, Pat. No. 5,367,789.

[51] Int. Cl.$^6$ .................................................. A61F 5/00
[52] U.S. Cl. .............................. 602/65; 602/27; 602/28
[58] Field of Search .................................. 602/27–29, 46, 602/65, 5

[56] References Cited

U.S. PATENT DOCUMENTS

| | | | |
|---|---|---|---|
| 3,527,209 | 9/1970 | Baker | 602/28 |
| 4,401,113 | 8/1983 | Incorvaia | 602/65 |
| 4,572,169 | 2/1986 | Mauldin et al. | 602/27 |
| 4,841,957 | 6/1989 | Wooten et al. | 602/27 |
| 5,007,416 | 4/1991 | Burns et al. | 602/27 |
| 5,020,523 | 6/1991 | Bodine | 602/27 |
| 5,036,838 | 8/1991 | Sherman | 602/44 |
| 5,176,624 | 1/1993 | Kuehnreich | 602/65 |
| 5,368,551 | 11/1994 | Zuckerman | 602/27 X |
| 5,370,133 | 12/1994 | Darby et al. | 602/27 X |
| 5,372,576 | 12/1994 | Hicks | 602/27 |
| 5,393,303 | 2/1995 | Shiono | 602/28 X |
| 5,403,265 | 4/1995 | Berguer et al. | 602/27 X |
| 5,425,701 | 6/1995 | Oster et al. | 602/23 |

Primary Examiner—Stephen R. Crow
Assistant Examiner—David R. Risley
Attorney, Agent, or Firm—Charles W. Chandler

[57] ABSTRACT

A medical boot includes a two piece boot body consisting of a lower flexible panel forming the sole portion of the boot body, and an annular flexible upper body joined to the peripheral edge of the lower panel so as to form a soft flexible protective wall around the toe and heel areas of the wearer's foot. Each panel includes a resilient foam core, an inner fabric covering on one face of the foam core, and an outer fabric covering on the other face of the foam core. The inner fabric covering has a relatively soft short nap surface having wicking properties for capturing perspiration that may accumulate on the wearer's foot. The outer fabric covering is a fibrous fastener material containing repeating contiguous miniature loops capable of interlocking connection with fastener patches carried by two strap formed integrally with the upper panel, such that the straps are enabled to hold the boot on the wearer's foot. Edge areas of the fabric coverings are heat fused together to form a seal around the foam core in the upper panel.

3 Claims, 9 Drawing Sheets

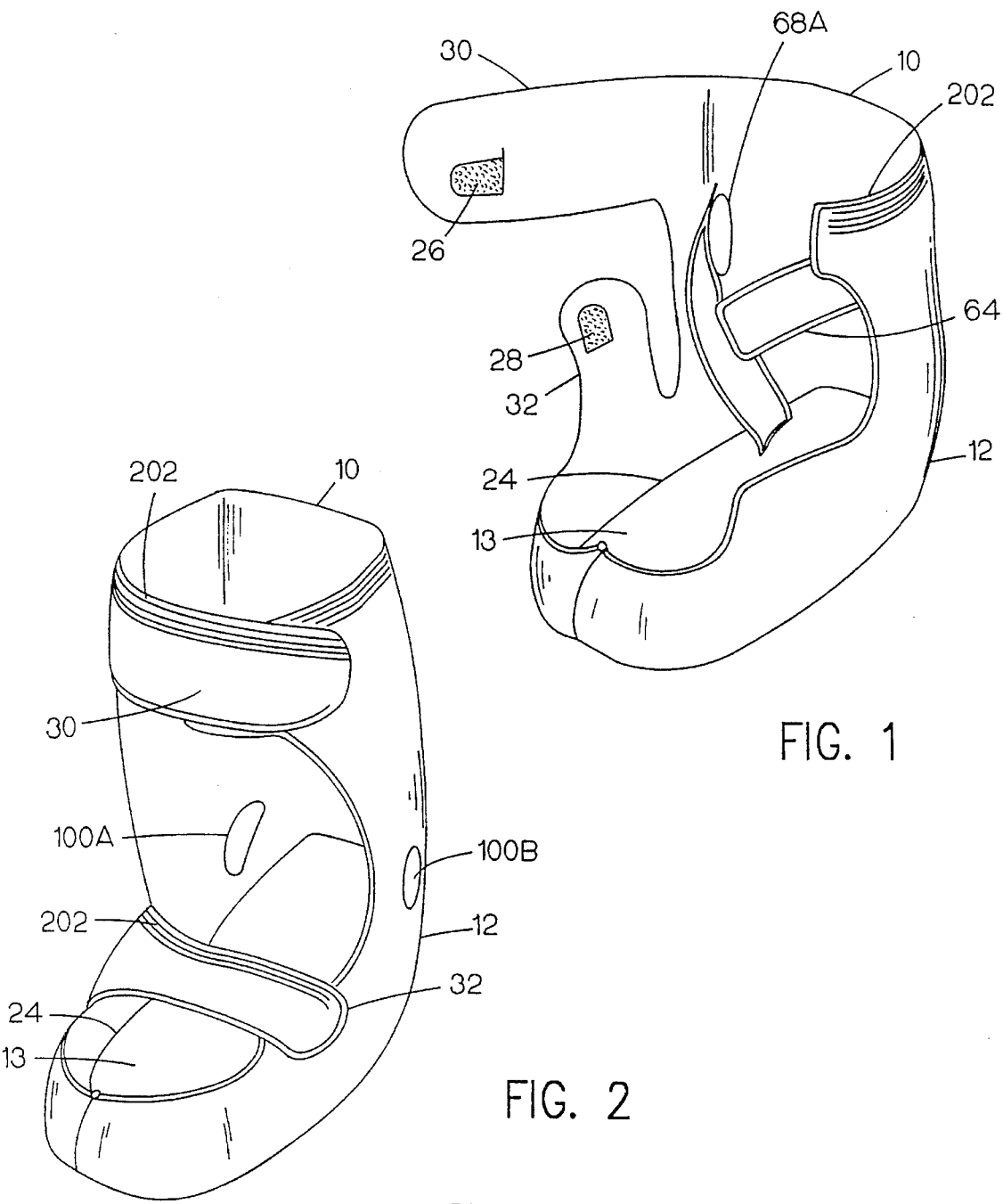
FIG. 1
FIG. 2
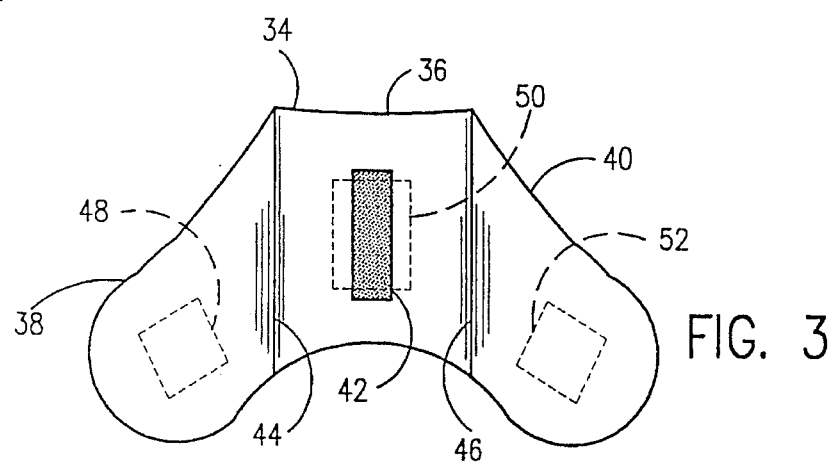
FIG. 3

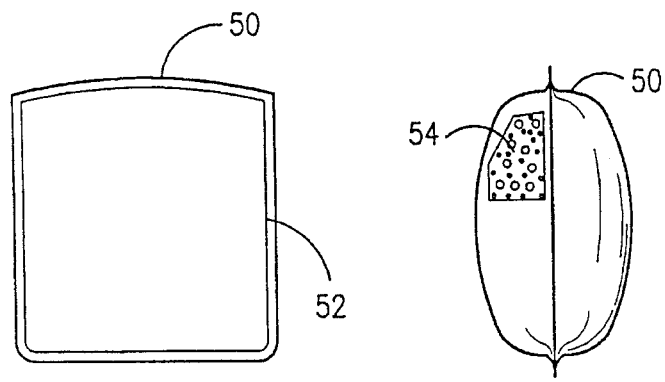
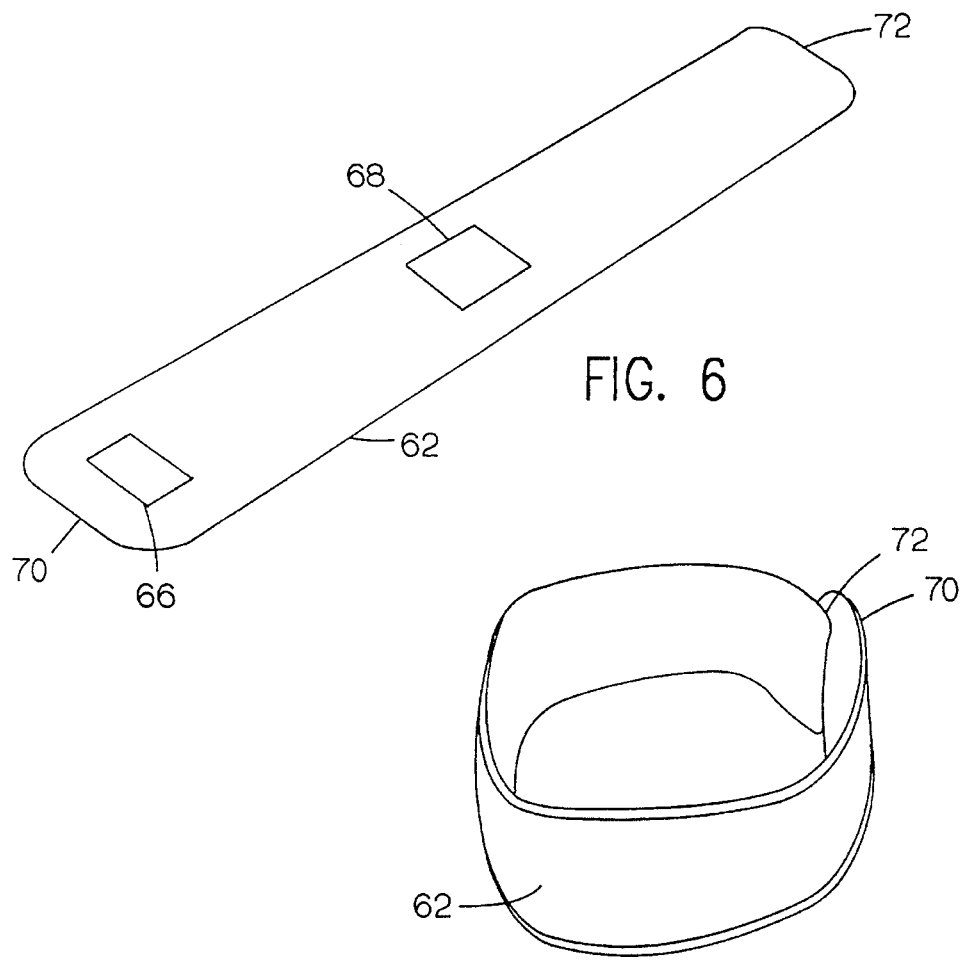

PROTECTIVE MEDICAL BOOT AND ORTHOTIC SPLINT

CROSS REFERENCE TO RELATED APPLICATION

This application is a continuation-in-part of my application Ser. No. 8/090,895 filed Jul. 12, 1993, for PROTECTIVE MEDICAL BOOT AND ORTHOTIC SPLINT and since issued as Letter Patent No. 5,367,789 on Nov. 29, 1994.

BACKGROUND OF THE INVENTION

The medical boot disclosed in my co-pending patent application provides many special advantages over competitive products. The boot is formed of a soft, flexible, compressible, foam core with inner and outer layers of brushed tricot. The brushed tricot is characterized by a continuous layer of small loops which make the material compatible with Velcro type fabric hook fastener means.

Patients who wear the boot have very, sensitive skin. One purpose of the boot is to relieve pressure or contact between the inner surface of the boot and the user's heel area. The closed nature of the boot makes it difficult to observe the condition of the patient's heel except through a slot in the bottom rear base of the heel.

The core and the inner and outer layers of my prior boot are stitched around their upper edge with an over edge binding to strengthen the perimeter against fraying as well as to provide a seam.

My prior boot could also be worn in some cases by a patient who desired to walk while wearing the boot. The outer sole of the boot comprised a layer of a Velcro compatible material, however, it was not especially useful for walking because on its relatively soft nature.

SUMMARY OF THE INVENTION

One of the purposes of the invention is to provide an improved medical boot which may be used either alone or together with an adjustable orthotic splint.

The boot described in my co-pending application employs straps for closing the boot over the patient's foot. The straps use a hook type fabric fastener. The outer boot cover has a continuous surface of small loops which form a releasible attachment for the straps and other boot components.

However, I found that a superior material is available for the inner cover. The tissue of the patient's skin normally is very delicate and can be either granulated and/or damaged by a coarse material such as foam rubber, sheepskin or KODEL, because such materials have fibers that can get into open wounds. I have found that employing a soft wicking material such as Nylon type 6, polyester, and polyurethane foam Loop 3973 laminate available from Velcro USA Inc., offers special advantages because it does not have any surface fibers that can get into an open wound. The material drastically reduces any shear force on the user's tissue. Further the material has superior wicking characteristics. It keeps moisture away from the skin of the lower leg and foot thereby keeping the foot and leg at a normal thermic temperature, Further, I have found that the user's skin tissue can be further protected if the seams around the edges of the boot and the straps normally formed by a stitching technique, are eliminated by using heat and pressure to fuse the outer edges of the boot body. Stitched seams which might impede capillary flow and create tissue trauma are eliminated. The heat-fused edges do not disturb the softness of the internal cover material.

My improved boot employs a pair of lateral slots along opposite sides of the heel area so that the caregiver can readily view the location of the user's heel in the boot as well as the condition of the heel tissue. The additional slots provide additional ventilation, reducing heat build-up.

The edges around the outside of the top of the boot and the integral foot straps have a ribbed contour formed during the heat fusing process which can be trimmed to reduce the height of the boot, leaving a low profile against the calf of the leg. The height of the boot can be reduced about 1" without interfering with the fused joint between the boot materials.

A still further object of the invention is to provide an improved boot that the user can wear while walking. The invention employs a removable external sole. The sole has a rubber-like construction that is easy to walk on. The sole has hook fabric fastener strips that can be readily attached to the Velcro compatible material on the outside bottom of the boot. The sole can be easily disengaged when the patient is in bed, keeping the bottom of the boot clean and dry. This represents an improvement over other products that require screws or clips to hold a removable sole in position.

A separate cushion comprising a generally, rectangular, compressible body about 4"×4½, with a pair of foldable wings, is also employed. Hook fastener patches permit the cushion to be mounted in a variety of supporting positions either inside or outside the boot.

The cushion body and the wings each have an internal sac filled with air/water/gel combination as the weight-bearing material. The cushion can be used in multiple positions within the interior or the exterior of the boot structure. It is particularly useful because it can be adjusted to custom-fit the patient's heel and foot area. It can be placed beneath the leg to form a well in the boot that removes pressure from under the heel. The wings protect the lateral and medial malleolus (bony ankle prominence), cushioning and thereby reducing pressure in these areas.

For the recumbent patient, the cushion can be used in the ankle area of the boot for cushioning the plantar surface of the foot, relieving unwanted pressure, forming a well at the bottom of the heel, or taking pressure away from the toes or the metatarsal area. The wings of the cushion relieve pressure from the side surfaces of a patient lying on lateral or medial aspects.

The cushion uses a flexible plastic container containing a gel mixed with air and water. The gel mixture provides a soft weight-bearing article having special properties for retaining heat or cold. Used alone, the container can be heated in a microwave oven or warm water. It retains such heat for an extended period of time. Similarly, it remains cool for a long period of time when cooled in a refrigerator. These properties can be used in many therapeutic devices for stimulating circulation in a patient's limb.

The boot has a leg strap with a fabric hook fastener patch sewn at one end which permits that end to be connected to the boot at an adjusted position around the calf area, thereby providing a secure fit of the leg extremities. The strap accommodates any size leg, such as a patient with a thin leg or a leg enlarged with edema.

The boot has a foot strap with a hook fastener sewn at one end which allows the fabric hooks to bite into the boot covering. The foot strap can be mounted across the in-step area of the foot portion of the boot to allow for adequate space for foot dressings and ventilation. The foot strap can also be pulled across the foot at a greater degree which reduces the open toe design thereby minimizing heat loss or promoting reflex vasodilation which is especially important to a diabetic patient. The foot strap can be folded back for visual inspection of the patient's foot for pulse checks or skin color inspection or it can be used in the open position for a foot cradle. It also dissipates excessive heat and perspiration.

A removable ¾" soft foam insole or liner having brushed tricot laminated on the bottom side, and a soft wicking material on the side contacting the user's tissue, covers the floor of the boot. The soft insole can be washed and air dried.

The boot also includes a plastic, substantially rigid insole, about ¼" thick, disposed inside the boot. The floor of the boot is connected to the hard insole by patches of fabric hooks, to securely hold the hard insole in position. The hard insole can be separated from the body of the boot as well as from the soft insole to launder the boot and the soft insole.

A flexible white styrene insole, about 0.100" thick is used when the ¼" rigid insole is not used.

An adjustable orthotic splint positively supports the patient with correctable foot drop, with or without neuromotor deficit. In addition, the splint combined with the boot, addresses conditions associated with foot and leg contractures, pressure ulcers and skin necrosis of the heel, leg and foot. The splint satisfies patient compliance for comfort, safety and effectiveness while offering the caregiver a complete system that requires no screw driver, screws or other such fasteners, thereby making the splint easy to use.

The splint includes a splint bar, about 11" long, which is supported on the outside of the boot, back of the ankle. A pair of fabric hook patches connect the splint bar to the boot. The lower end of the bar has a pair of spaced lugs with a group of pin-receiving openings. A right-angle hinge member has one end mounted between the lugs at an adjusted angle. The arm at the opposite end of the hinge member is then disposed at an adjusted angle with respect to the splint bar. The arm has a tongue structure that can be inserted in the slot in the heel of the boot into a complementary groove structure on the heel end of the hard insole.

The hard insole can thus be adjusted in any of three positions by a positioning pin to create either a normal position in which the patient's foot is at right angles to the patient's ankle, a second position in which the hard Insole and the foot are dropped 30° from their upright position, or in a third position in which the hard insole is supported toward the user 10° from the vertical position, when the user is lying on his back. These positive settings can be achieved quickly and simply which is useful for the recumbent patient with a flaccid syndrome (foot drop). The splint is useful for conveniently varying the foot angle at prescribed intervals to change the attitude of the foot and leg muscles to avoid or correct contractures.

A stabilizing bar, mounted on the mid-section of the splint bar, can be swivelled between a position parallel to the splint bar, or a stabilizing position at right angles to the user's leg to support the foot. The stabilizing bah thus controls the rotation/anti-rotation, inversion/eversion of the hip, leg and foot.

A locking bridge connects the stabilizing bars of a pair of splints for bilateral abduction or adduction to correct rotation and proper alignment of both the patient's legs.

Still further objects and advantages of the invention will be readily apparent to those skilled in the art to which the invention pertains upon reference to the following detailed description.

DESCRIPTION OF THE DRAWINGS

The description refers to the accompanying drawings in which like reference characters refer to like parts throughout the several views, and in which:

FIG. 1 illustrates a preferred medical boot in the open position;

FIG. 2 shows the boot in the closed position;

FIG. 3 illustrates the foldable cushion;

FIG. 4 is a view of a typical air/water/gel sac received in the three parts of the foldable cushion;

FIG. 5 is a side view of the sac of FIG. 4;

FIG. 6 is a view of a preferred ankle strap in the laid-out position;

FIG. 7 shows the strap in the closed position;

DESCRIPTION OF THE PREFERRED EMBODIMENT

Referring to FIGS. 1 and 2, a preferred medical boot 10 comprises an upper annular flexible panel 12 and a bottom flat flexible sole panel 13. The general configuration of the boot is described in my co-pending application and is formed from a multi-layer sheet containing the profile of the upper panel and the sole from which both are cut.

Figure 17:
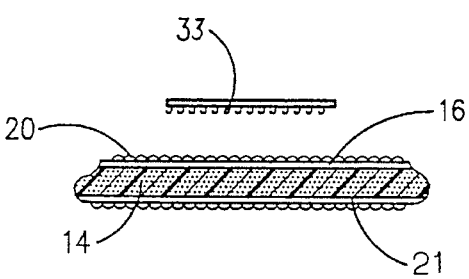
FIG. 17 shows a typical cross-section of the boot material.

Referring to FIG. 17, both the upper boot portion and the sole are formed of an elastomeric, shape-retaining material, such as a soft, flexible compressible, open-core polyurethane foam core 14, and an outer layer 16 of an ultra-smooth, soft, non-allergenic cloth such as brushed tricot. This type of fabric is characterized by a continuous layer of small loops 20 which makes the material compatible with fabric hook fastener means such as Velcro fasteners. The entire outer cover of both the upper portion of the boot and the sole have a brushed tricot covering so that a patch of a Velcro-type hook material can be connected in any position on the boot.

Still referring to FIG. 17, the inner cover material 21 is formed of a self-wicking material such as nylon type 6 polyester and polyurethane foam loop 3973 laminate provided from Velcro USA Inc. Such material does not have any surface fibers that can get into a patient's wound, but has excellent wicking properties by attracting any perspiration that may accumulate on the user's tissue. The inner cover material is available from Dela, Inc., 175 Ward Avenue, Ward Hill, Mass. The material has no fleece, paper fibers or vinyl requiring cornstarch powder. It reduces shear and effectively controls skin moisture.

Figure 25:
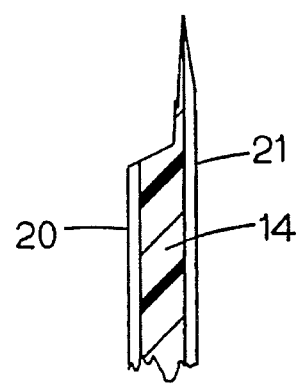
FIG. 25 is an enlarged cross-sectional view showing the heat fused compressed edge of the boot.

Referring to FIG. 25, the upper panel has an exposed edge area defined by mating surfaces of the inner fabric covering 21 and the outer fabric covering 20, these two coverings heat-fused together to form a seal around the foam core 14. As further shown in this figure, the mating surfaces of the fabric coverings 20,21 extend beyond the associated edge of the foam core 14, whereby the surface of the edge facing the wearer's body forms a planar continuation of the inner surface of the panel. The entire edge of the upper portion of the boot is heat fused and compressed together, preferably a width of about ¼" from the extreme edge. The thickness of the boot core is reduced in the fused area as the boot materials are joined and fused together. The interior fused edge of cover 21 of the boot still has a soft material in contact with the user's tissue.

Referring to FIG. 1, an over edge binding 24 is stitched around the inside seam between the sole and the upper portion of the boot. The floor seam does not come into contact with the user's foot.

The boot has two patches 26 and 28 of a hook-shaped fabric fastener near the outer end of leg strap 30 and the outer end of foot strap 32, respectively. The fabric hook fastener material may be a Velcro fabric fastener and is characterized by a plurality of small fabric hooks 33, as can be seen in FIG. 17. Thus both boot straps with the patches of fastener material can be connected to the opposite side of the boot opening, as illustrated in FIG. 2, in any selected position. The location of the connection is not limited to the position of a matching patch.

The boot also employs a cushion 34, illustrated in FIG. 3, which is very similar in configuration to the cushion illustrated in my co-pending application. Cushion 34 has a central portion 36 and a pair of side panels or wings 38 and 40. The cushion is similar in construction to the boot, that is formed with an inner core of a flexible, compressible open cell polyurethane foam with an outside covering of a brushed tricot material, that is, a material having a continuous surface of closed loops, and an inside covering of the same wicking material as the boot.

A patch 42 of a Velcro fabric hook-type fastener material is attached to one side of a central portion 36. Central portion 36 has a somewhat rectangular configuration while side panels 38 and 40 extend at about a 45° angle from a pair of foldable parallel fold lines 44 and 46.

The central body portion and the two side panels each have an internal recess for receiving flexible plastic sacs 48, 50, and 52 respectively. A typical sac 50 is illustrated in FIGS. 4 and 5 and comprises a flexible, sealed, fluid-tight plastic container 52 about 3¾"×5. FIG. 5 shows the typical container partially broken away to show the internal air/water/gel material 54 which fills the plastic container. The gel is a material mixed with a combination of bubbles of air, water and the gel. The mixture gives a cushioning effect and also can be used to either warm or cool a patient's limb because of its ability to retain either heat or a low temperature for a long period of time. When used separately from the cushion, the sac can be heated either in a microwave oven or In warm water. Alternatively, it can be cooled in a refrigerator. I believe the bubbles of air and water in the gel change the heat-retaining properties of the gel. The gel mixture is available from Cold Ice, Inc., Oakland, Calif.

Sac 50 is illustrative of the sacs in the three portions of the cushion. Similar sacs may be employed in other parts of the boot. The sac is very compressible and soft and at the same time provides support to a user's limb placed on that portion of the cushion containing the sac.

Figure 18:
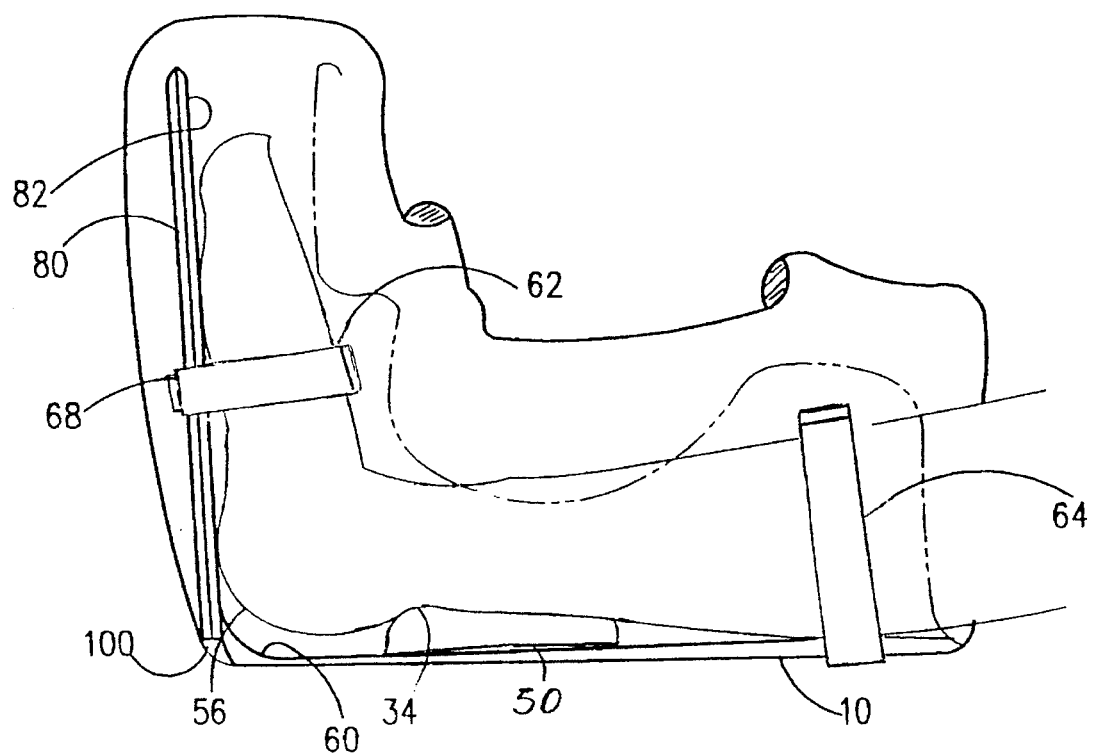
FIG. 18 is a view of the user's foot super-imposed over the outline of a boot, showing the relationship between the foot and ankle supported by the two straps and the cushion.

Cushion 34 can be readily connected to either the inside or the outside of the boot in any selected position. FIG. 18 illustrates the manner in which the user's foot 56 may be disposed on the cushion. The cushion can be adjusted according to the configuration of the user's ankle and leg to support the leg while providing a well 60 beneath the user's heel. Fastener patch 42 then maintains the cushion in the selected distance from the heel of the boot.

A pair of straps 62 and 64 are wrapped around the user's foot and leg. The two straps are similar in construction, each comprising the same type of inner and outer coverings as the boot. Strap 62 is illustrated in FIGS. 6 and 7. For illustrative purposes, the strap is 18¼" long, 2½" wide and has two patches 66 and 68 of a fabric hook type fastener. The two patches are preferably about 1½–2" wide. Patch 66 is located about ½" from the one end of the cuff; the other patch 68 is located about 8½" from the edge of patch 66. The arrangement is such that when one end 70 of the strap is coiled adjacent the opposite end 72, patch 66 forms a releasable attachment to the cover material adjacent end 70, as illustrated in FIG. 7. The other patch 68 is then on the inside of the strap to engage the outside of the boot as illustrated in FIG. 1. The ends of strap 62 are passed through slot means 68A into the boot.

Strap 62 is similar to strap 64, but shorter, and is wrapped around the user's foot and locked into position by fastener patch 68 which releasably locks with the bottom of the boot.

Figure 22:
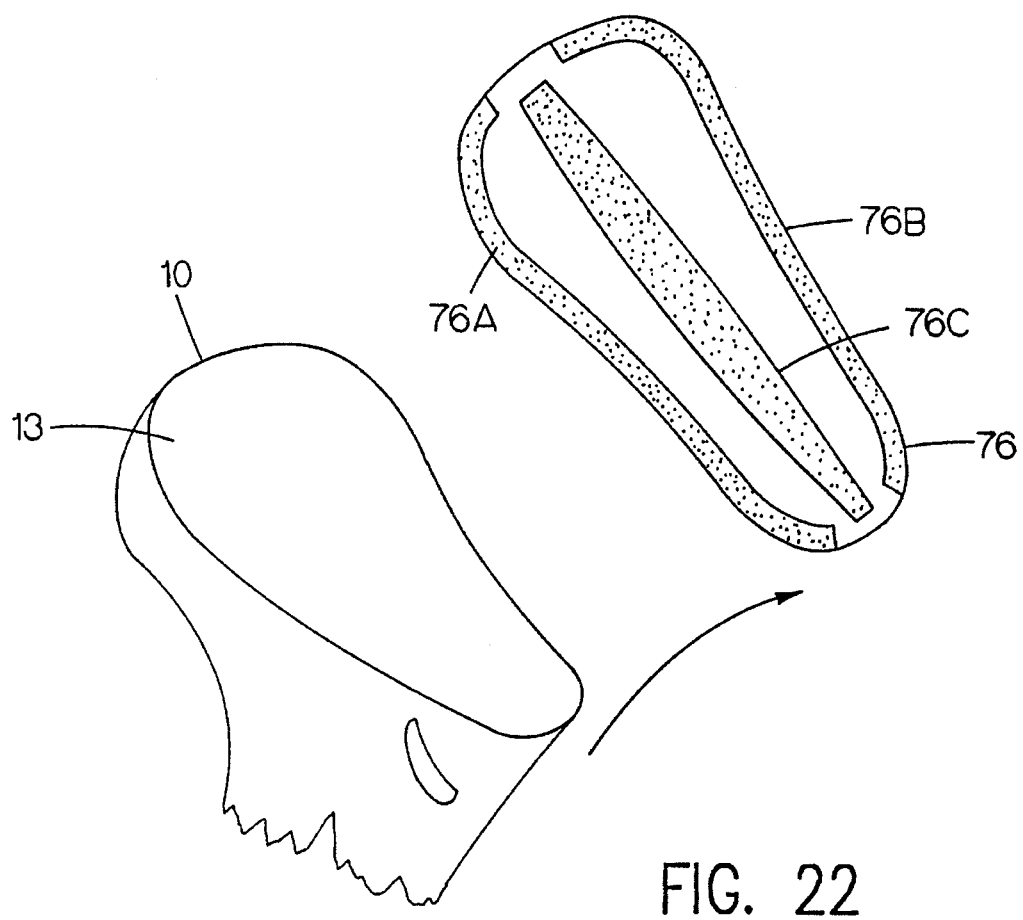
FIG. 22 is an exploded view of the external removable hard sole used for walking.

Referring to FIG. 22, a rubberized sole 76 is attached to the Velcro compatible covering on the bottom outside sole of the boot by fabric hook fastener to provide sufficient friction so that the user can walk with the boot on a smooth surface. In FIG. 22, numerals 76A, 76B and 76 reference non-slip rubber strips on the bottom surface of the exterior sole.

Figure 8:
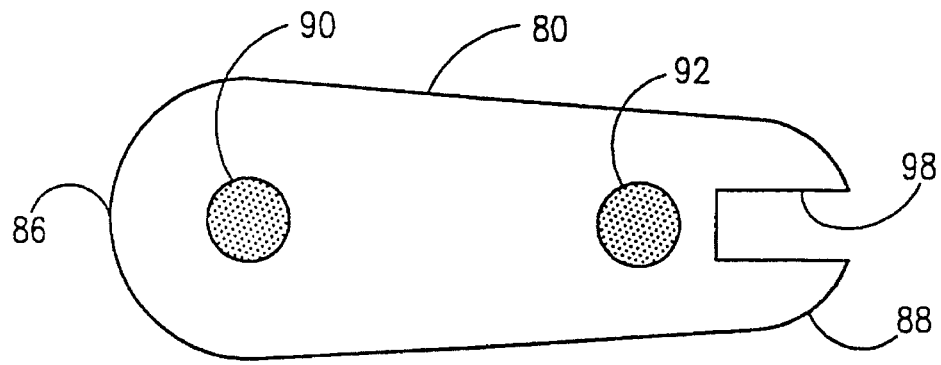
FIG. 8 is a plan view of the hard insole.
Figure 9:
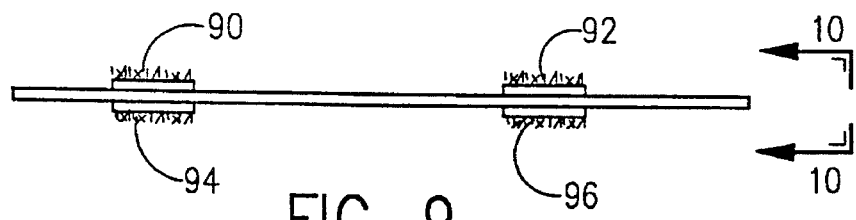
FIG. 9 is an edge view of the hard insole.
Figure 11:
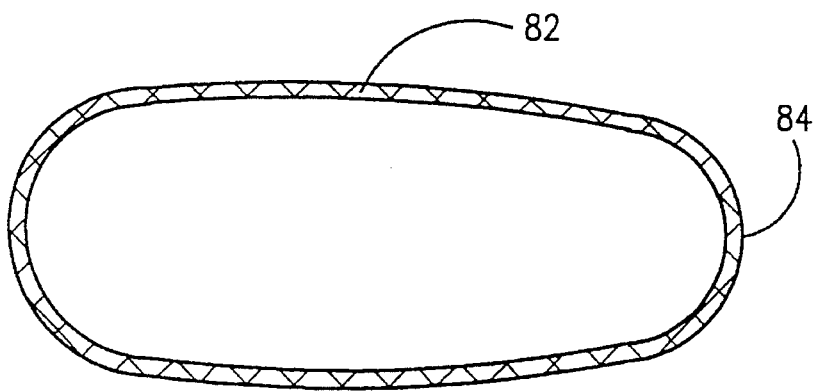
FIG. 11 is a plan view of the soft insole.
Figure 12:
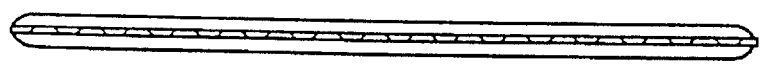
FIG. 12 is a side view of the soft insole.

A pair of insoles 80 and 82, illustrated in FIGS. 8 and 11 respectively, may be used in the boot. Insole 82 is soft, having an edge configuration slightly smaller than the bottom inside of the boot so that it can be inserted in the boot to protect the bottom of the user's foot. Insole 82 is made with the same construction as the boot, that is with a compressible inner liner, a brushed tricot cover on the bottom, a ½" wide heat sealed edge around its perimeter, and a self-wicking material on its top.

Hard insole 80 is formed of a relatively rigid polypropylene plastic material with an outside contour slightly smaller than soft insole 82 and a ¼" thickness. Insole 80 is intended to be inserted in the bottom of the boot and connected to the bottom of the soft insole.

Hard insole 80 has a toe end 86 and a heel end 88. Two patches of hook fabric fasteners 90 and 92 are attached to one side of the hard insole about 6" apart, along the center line of the insole. Each patch is about 1¼" in diameter.

A second pair of fabric fastener patches 94 and 96 are mounted on the opposite side of the hard insole in the same relative position as patches 90 and 92. Thus when the hard insole is placed in the bottom of the boot, lower patches 94 and 96 engage the fabric loops on the covering of the bottom of the boot to releasibly lock the hard insole in position.

Similarly when the soft insole is mounted on top of the hard insole, patches 90 and 92 releasibly lock the soft insole in position. The assembly can be readily removed from the boot for cleaning the insoles as well as the boot.

Figure 10:
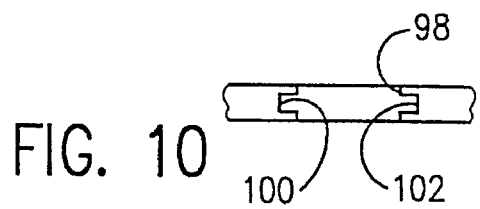
FIG. 10 is a view as seen along lines 10—10 of FIG. 9.

Referring to FIGS. 8 and 10, the heel end of the hard insole has a slot 98, 1" wide and 2⅜" deep. The side edges of the slot have opposed longitudinal grooves 100 and 102.

FIG. 18 shows the relative position of the hard insole with respect to the body of the boot. The boot also has a 1½" opening 100, with heat-fused edges along the seam between the upper portion of the sole of the boot. Opening 100 provides access to slot 98 of the hard insole as well as permitting a visual inspection of the user's heel without removing the boot.

The boot also has a pair of lateral curved slots 100A and 100B (FIG. 2) formed with heat sealed edges, on opposite sides of the boot in the area adjacent the user's heel. Slots 100A and 100B supplement opening 100 for permitting a visual observation of the user's heel for position and condition.

Figure 13:
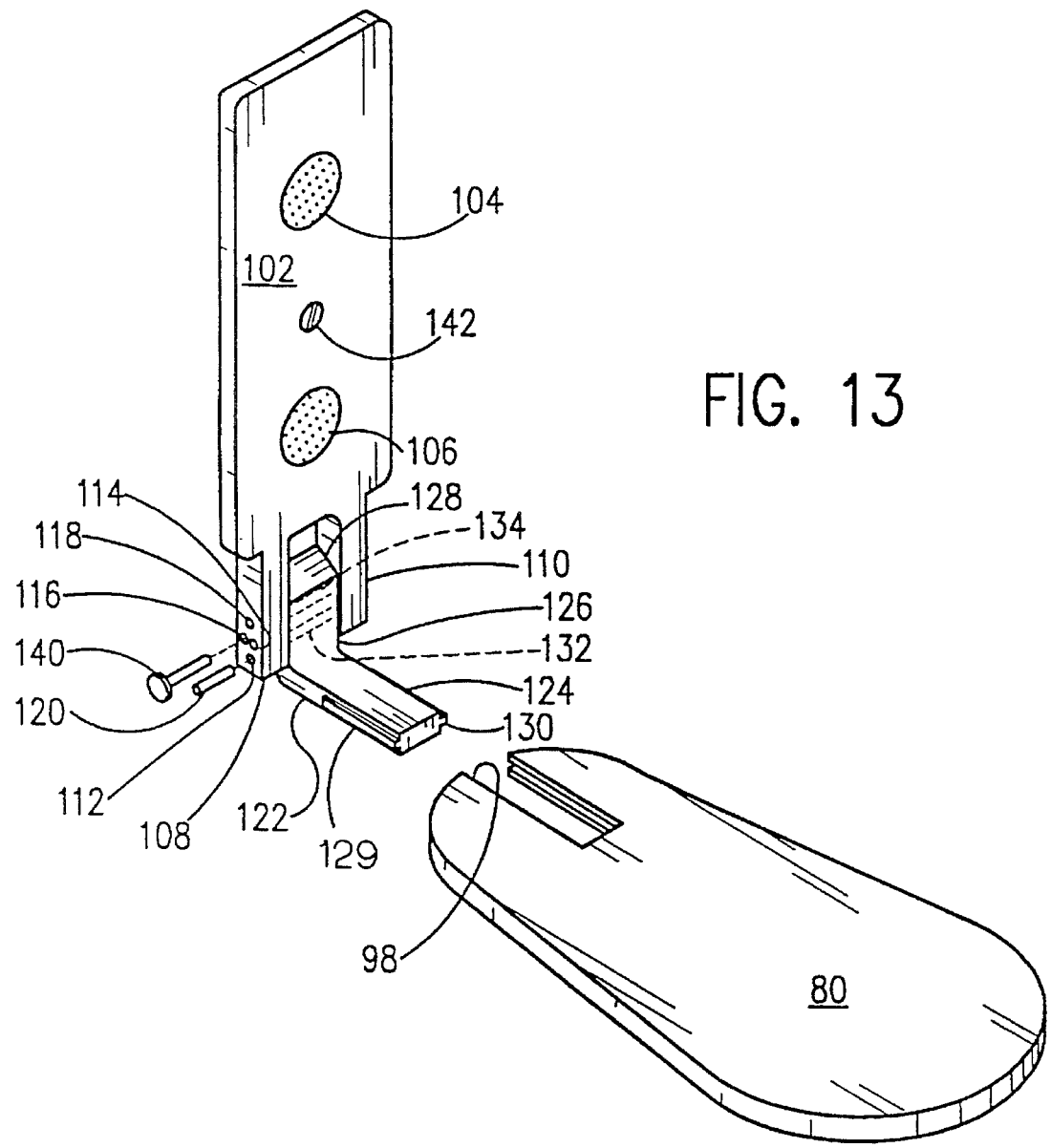
FIG. 13 is a partially exploded view of the adjustable splint and its relationship to the hard insole.

FIG. 13 illustrates splint bar 102 and its relationship to hard insole 80. Splint bar 102 is also formed of a rigid polypropylene material, 3" wide, 9" long, and ¼" thick. The inside face of the splint bar has a pair of 1¼" diameter hook fabric fastener patches 104 and 106 located about 3" apart. Patches 104 and 106 connect the splint bar to the outside back surface of the boot. Patches 104 and 106 can be readily attached to any suitable location on the boot cover.

Splint bar 102 has a pair of parallel lugs 108 and 110 which are 2½" long and spaced 1¾" apart. The two lugs have four pairs of aligned openings 112, 114, 116 and 118. A hinge pin 120 is slideably received in aligned hinge openings 112 with a slight friction fit so that it remains in the opening unless pushed out.

An angular hinge member 122 connects the splint bar to the hard insole. Hinge member 122 has a leg 124, and a second leg 126 disposed at right angles to leg 124. Leg 124 has about 3¾" a length permitting it to be inserted in heel opening 100 of the boot. The opposite side edges of leg 124 have longitudinal tongues 129 and 130 slideably received in grooves 100 and 102 of the heel end of the hard insole, forming a tongue and groove connection between the hinge member and the hard insole. The tongues are frictionally retained in the grooves so that it takes some effort to pull the hinge member from the hard insole heel opening.

Short leg 126 has about a 2" overall length including a tapered toe 128. Leg 126 has a pair of spaced, parallel, transverse openings 132 and 134.

When the short leg of the hinge member is inserted between the two lugs of the splint bar, opening 132 is aligned with openings 112 in the lugs. Hinge pin 120 is then inserted through the openings in the lugs and the hinge member so that the hinge member is pivotable with respect to the splint bar. The other opening 126 can then be aligned with either openings 114 or 116 by swinging the hinge member.

Figure 19:
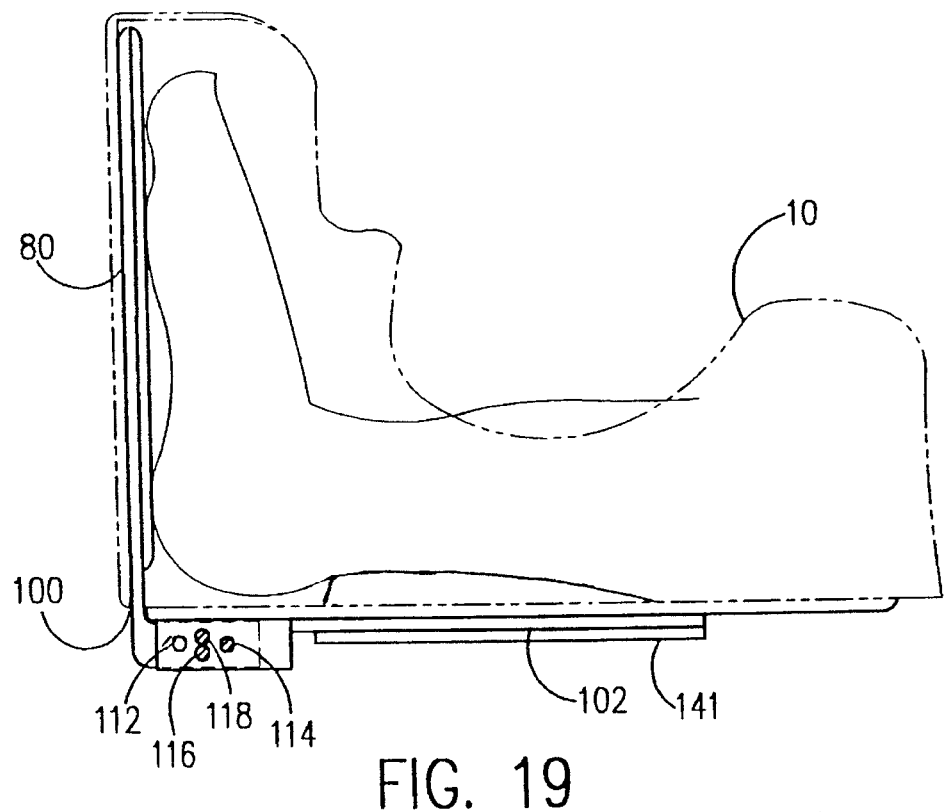
FIG. 19 is a view showing the manner in which the splint bar and the hard insole support the foot in the normal foot position.

Referring to FIGS. 13 and 19, when opening 126 is aligned with openings 116, a locking pin 140 is inserted in the aligned openings to connect the hinge member and the lugs in such a manner that the hard insole is disposed at a 90° angle with respect to the plane of the splint bar.

Figure 20:
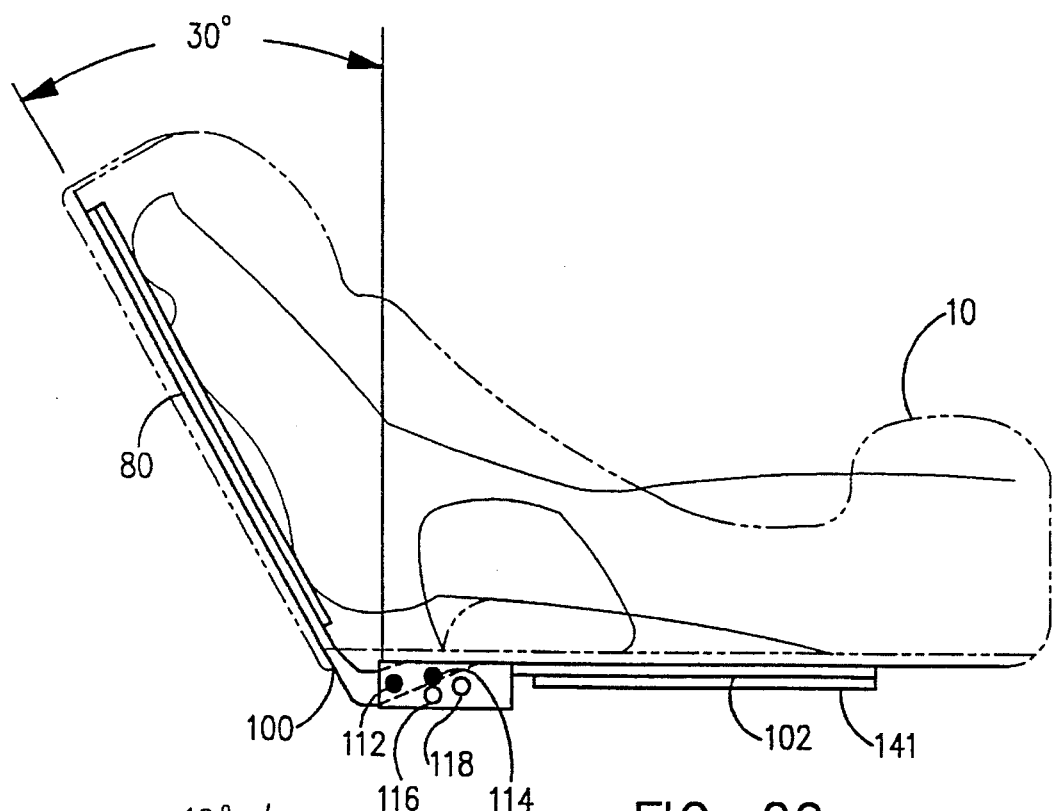
FIG. 20 is a view showing how the splint bar and the hard insole cooperate to support the foot in an extension position of about 30° from the vertical.

Referring to FIG. 20, when the hard insole is swung to align opening 126 with openings 114 in the lugs, locking pin 140 can be inserted in openings 114 and 126 to lock the hard insole in a position 30° from the normal vertical foot position so that the foot has an extension of 30°.

Figure 21:
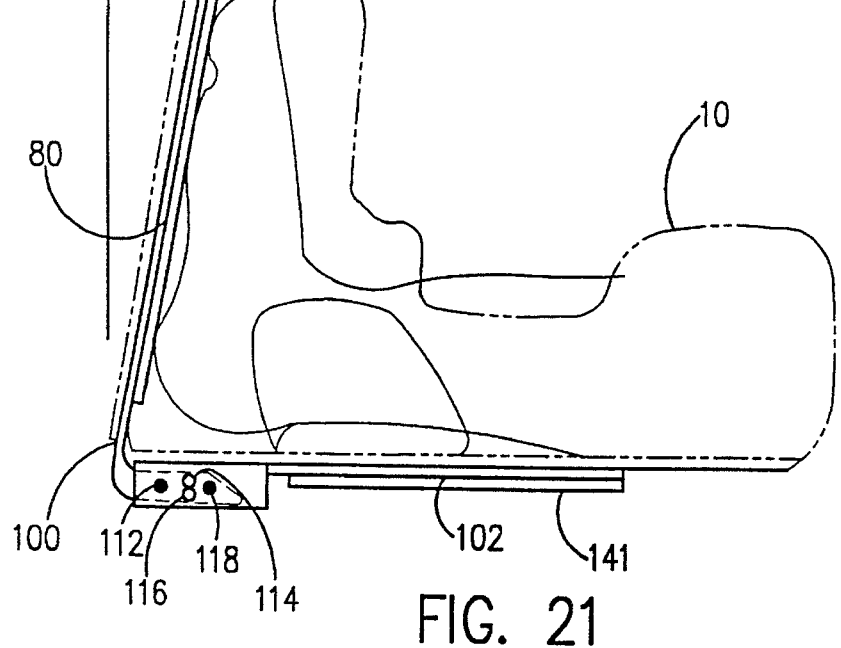
FIG. 21 is a view showing how the splint bar and the hard insole cooperate to support the foot in the flexion position of about plus 10°.

Referring to FIG. 21, if the hinge member is pivoted toward the splint bar, to position toe 128 beneath opening 114 as illustrated in FIG. 21, and the locking pin is inserted in openings 118, the hard insole will be disposed in a flexion position, that is about 10° from the right angle position. The user's foot prevents the hard insole from moving clockwise toward the 90° position, while the locking pin prevents the hard insole from moving counterclockwise toward the 90° position, as viewed in FIG. 21.

Figure 14:
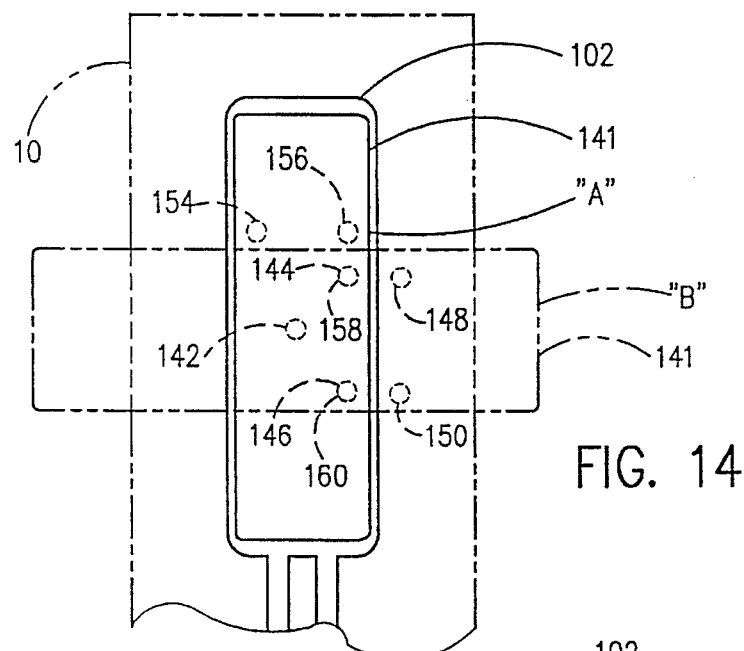
FIG. 14 is a view of the splint bar and the stabilizer bar, showing the stabilizer bar in its' stabilizing position in phantom.
Figure 16:
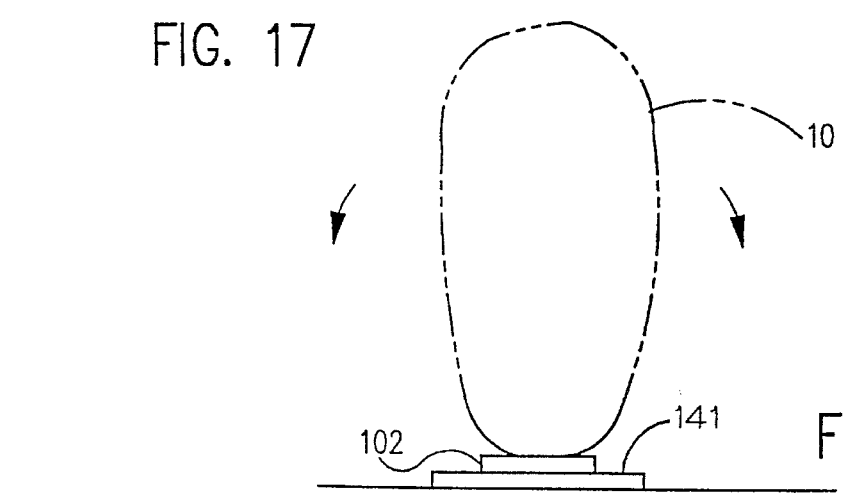
FIG. 16 is a view illustrating the manner in which the stabilizing bar prevents the boot from rolling over from its upright position.

Referring to FIGS. 14 and 16, a stabilizer bar 141 is connected to the splint bar. The stabilizer bar has essentially the same width as the splint bar, is slightly shorter than the splint bar and is ¼" thick. The splint bar and the stabilizer bar are shown in a face-to-face relationship. Pin means 142 connect the stabilizer bar to the splint bar so that the stabilizer bar can be moved from a parallel position illustrated at "A", to an outer position illustrated at "B", which is at right angles to the splint bar and the user's leg. Both the stabilizer bar and the splint bar have a width substantially less than the width of boot 10.

Figure 15:
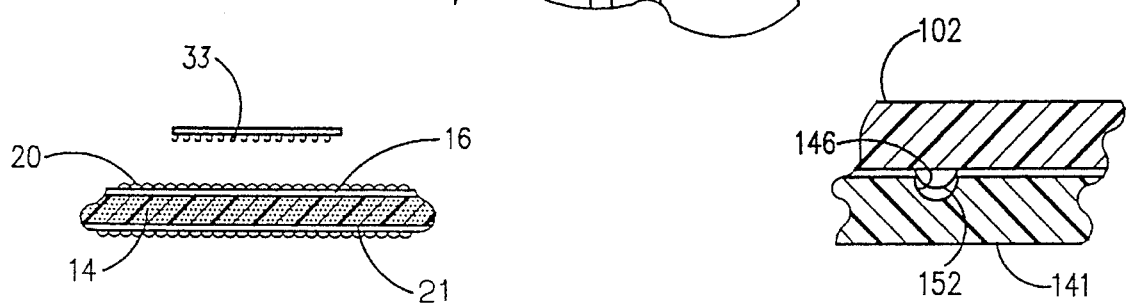
FIG. 15 is a fragmentary, enlarged sectional view of a typical locking knob for the stabilizer bar.

The stabilizer bar has four recesses 144, 146, 148 and 150. A typical recess 146 is illustrated in FIG. 15. A typical rounded nub 152 is also illustrated in FIG. 15. A similar nub is located at positions designated 154, 156, 158 and 160. The recesses and nubs are located on the splint bar and the stabilizer bar to releasibly lock them in either position "A" or in position "B".

Referring to FIG. 16, the stabilizer bar in its outer position extends beyond the side profile of the boot in such a manner that when the patient is lying in a supine position, the stabilizer bar through its connection with the splint bar and the hard insole prevents the user's foot from swinging toward either the right side or the left side in the direction of the arrows illustrated in FIG. 60. The stabilizer bar prevents the boot from swinging about the side edges of the splint bar.

Figure 24:
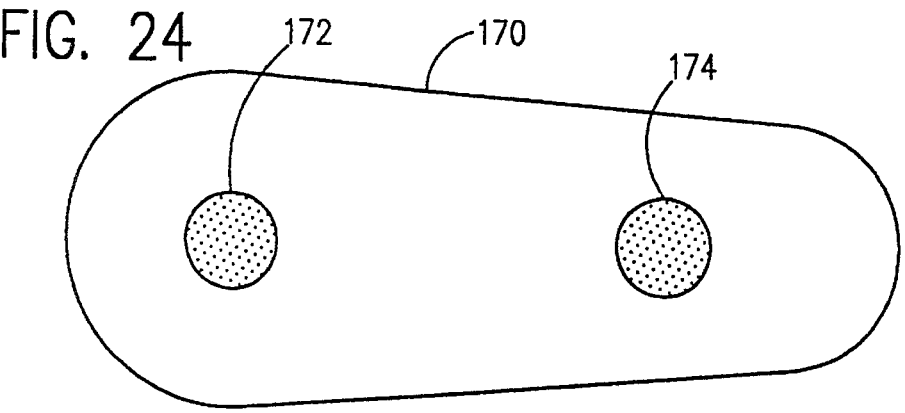
FIG. 24 illustrates a flexible plastic insole used when the hard insole is not being used.

Referring to FIG. 24, a flexible, semi-rigid insole 170 having generally the same configuration as hard insole 80, but without slot 98, is used when the patient does not use either the splint or the hard insole. Insole 170 is about, 0.100" thick and formed of a white styrene plastic. It has hook fabric fastener patches 172 and 174 on both of its sides for connection to the boot bottom and the soft insole.

Figure 23:
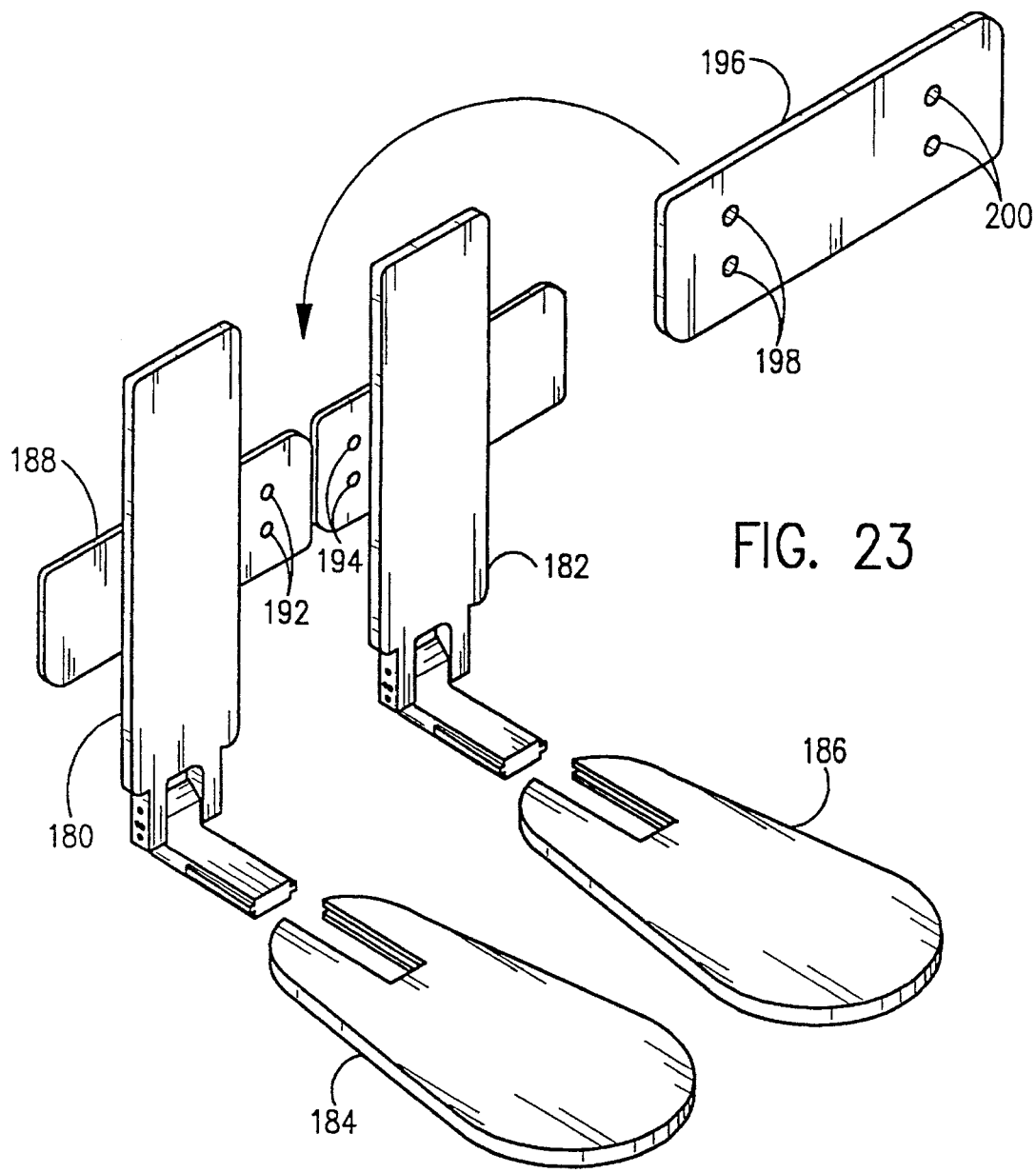
FIG. 23 is an exploded view showing how two splints are connected by a bridge member.

Referring to FIG. 23, a pair of splint bars 180 and 182, identical to splint bar 102 may be used for both feet of a patient. The two splint bars are adapted to be connected to a pair of hard insoles 184 and 186, respectively. The hard insoles are identical to hard insole 80.

The two splint bars support a pair of stabilizer bars 188 and 190, respectively. A rigid bridge bar 196, having the same width and thickness as the stabilizer bars may be connected to the stabilizer bars, in their open positions illustrated in FIG. 23. Nubs 198 mate with recesses 192, and nubs 200 mate with recesses 194 to releasibly lock the stabilizer bars in their open position. The bridge bar prevents the two stabilizer bars from swinging toward one another, and cooperate in keeping the user's feet from moving toward one another. The integrated structure locks the patient's feet together in a supported position.

Referring to FIGS. 1 and 2, the upper edges of the boot and the straps are heat sealed at a distance of about 1⅜" from the outer edge and formed with a series of five raised ridges 202, each about ⅛" wide, with a compressed area between each pair of ridges. This configuration provides thin areas that can be cut to reduce the height of the boot for patients having shorter legs. The height of the boot can be readily reduced about 1" while retaining the edges of the boot in their heat sealed connection. Similarly, the upper edges of both the integral straps and the separate straps have a similar configuration so that they can have their width readily reduced.

Thus it is to be understood that I have described an improved medical boot that can be used to support the user's foot in multiple positions as well as preventing foot-drop and pressure sores. The improved medical boot employs a cushion that can also be used in multiple positions within either the interior or the exterior of the boot structure. The cushion readily adjusts to custom fit the patient's heel and foot area to the boot, and can be placed in the boot near the heel to form a well, removing pressure from the back of the heel. The wings of the cushion protect the bony ankle prominence thereby greatly reducing pressure areas. The boot can be used for either a recumbent or an ambulatory patient. For the patient lying on the lateral or medial aspects, the wings of the cushion take pressure away from the sides of the user's limb. One of several air/water/gel sacs can be used and adjusted in various positions in the interior of the boot structure.

The boot and the cushion can be used in conjunction with a splint at the plantar surfaces of the user's leg to increase or reduce friction. Employing the boot covering with a continuous loop construction provides means for connecting integral boot straps 30 and 32 in any suitable position around the calf area thereby providing a secure fit of the leg extremity. The straps accommodate any leg size, either a thin leg or a leg enlarged with edema. Further, the straps because of their adjustability, provide room for adequate foot dressings and ventilation. They can be pulled across at a greater degree to reduce the open-toed design thereby minimizing heat loss. The straps can be folded onto the back of the boot for convenient visual skin color inspection, or the boot can be used in the open position as a foot cradle. The straps can be opened to permit the boot to dissipate excessive perspiration.

The soft insole covers the entire floor seam of the main body of the boot. It can be washed and air dried. It is attached to the hard insole by the fabric fastener patches.

The hard Insole also has a large exposed plastic surface with the patches fastened to the plastic by a high temperature adhesive. The patches also function to secure the soft insole in a position so that it can be separated from the body of the boot for laundering the boot and/or insole can be laundered.

The internal straps can be adjusted to a comfortable position while securing the leg to the inside structure of the boot. The leg strap can be adjusted up or down along the inside wall of the boot, avoiding abrasion of any existing wound or ulcer which may be present on the leg. The foot strap keeps the foot in proper alignment in the boot. The foot strap can be adjusted to a comfortable position according to the configuration of the patient's foot, and can be moved down along the plantar surface of the foot, avoiding irritating any existing wounds or ulcer conditions.

The splint is a multi-functional orthosis providing a positive setting for a patient with a correctable foot drop, or without neuromotor deficit. In addition, the splint, in conjunction with the boot, addresses conditions associated with foot and leg contractures, pressure ulcers and skin necrosis of the heel, leg and foot, and satisfies patient compliance for comfort, safety and effectiveness. The positive settings of the hard sole with a splint bar are achieved simply and quickly at the hinge by aligning the holes to the desire angle and inserting the locking pin. The splint bar can be easily removed from the patient. Further, it can be adjusted to vary the foot angle at prescribed intervals to change the attitude of the foot and leg muscles to correct contractures.

The stabilizing bar stabilizes the integrated rigid insole, thus controlling rotation or anti-rotation, inversion-eversion of the hip, leg and foot. A locking bridge can also be used with two splints for bi-lateral adduction or adduction.

Having described my invention, I claim:

1. A medical boot for orthotic or wound-care applications comprising, a two piece boot body that comprises a soft flexible upper panel, and a soft flexible lower panel joined together to form a protective boot around the wearer's foot and lower leg:

said lower panel including a peripheral edge defining the sole of the boot body;

said upper panel having a lower-edge coextensive with the peripheral edge so that the upper panel is adapted to surround the foot of the wearer, including the wearer's toe;

said upper panel comprising a front side portion extending upwardly from the front and side edges of said sole, said front side portion defining an opening exposing substantially the entire upper surface of the wearer's foot;

said upper panel further comprising a rear portion extending upwardly from the rear edge of said sole to partially surround the wearer's ankle and calf, leaving substantially the entire frontal surface of the lower leg and ankle exposed;

each of said panels comprising a resilient foam core, an inner fabric covering on the foam core surface facing the wearer's body, and an outer fabric covering on the foam core surface facing away from the wearer's body;

said inner fabric covering having a soft short nap surface having wicking properties for capturing perspiration that may accumulate on the wearer's body;

said outer fabric covering comprising a continuous outer surface containing repeating contiguous miniature loops capable of being interlocked with fibrous hook fastener materials;

said upper panel having an integral leg strap adapted to extend across the front surface of the wearer's leg, and an integral foot strap adapted to extend across the upper surface of the wearer's foot;

each of said straps having an inner surface that is a smooth continuation of the contiguous panel surface;

each of said straps having a patch of fibrous hook fastener material on its inner surface adapted to adhere to mating surface areas of the outer covering on the upper panel, for retaining the boot body on the wearer;

said upper panel having an exposed edge area defined by mating surfaces of the inner and outer fabric coverings heat-fused together to form a seal around the associated foam core; and said mating surfaces of the fabric coverings extending beyond the associated edges of the foam core, whereby the surface of said exposed edge area facing the wearer's body forms a planar continuation of the associated panel inner surface.

2. The medical boot of claim 1, and further comprising a rigid exterior sole releasably attachable to the lower exterior face of the sole on the boot body; said exterior sole having a rubberized non-slip lower surface, and an upper surface; and strips of fibrous hook fastener material carried on the upper surface of said exterior sole can be detached from the boot body or secured to the boot body when it is desired to use the medical boot for walking purposes.

3. A medical boot for orthotic or wound-care applications comprising a soft flexible boot body that includes a first lower panel defining the sole of the boot, and a second upper annular panel defining an upright portion of the boot;

- each of said panels comprising a resilient foam core, an inner fabric covering on said core having wicking properties, and an outer fabric covering on said core having a loop fastener surface;

- said upper annular panel being adapted to partially surround the wearer's foot and calf including the wearer's toes, said panel defining an opening exposing substantially the entire upper surface of the wearer's foot and substantially the entire frontal surface of the wearer's lower leg and ankle;

- said upper annular panel having an integral leg strap adapted to span the exposed frontal surface of the wearer's leg, and an integral foot strap adapted to span the exposed upper surface of the wearer's foot;

- each of said straps having a patch of fibrous hook fastener material adapted to interlock with the outer surface of said upper annular panel; and

- said upper annular panel having an exposed edge defined by mating surfaces of the inner and outer coverings heat-fused together, to provide a smooth uninterrupted inner surface facing the wearer's skin.

* * * * *